(12) United States Patent
Steinert et al.

(10) Patent No.: US 12,062,956 B2
(45) Date of Patent: *Aug. 13, 2024

(54) ELECTROMAGNETIC ROTARY DRIVE, A CENTRIFUGAL PUMP AND A PUMP UNIT

(71) Applicant: Levitronix GmbH, Zürich (CH)

(72) Inventors: Daniel Steinert, Bülach (CH); Thomas Schneeberger, Bern (CH); Thomas Nussbaumer, Zürich (CH); Marcel Stettler, Lenzberg (CH); Jonas Ginė, Stadel (CH)

(73) Assignee: LEVITRONIX GMBH, Zürich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/710,420

(22) Filed: Mar. 31, 2022

(65) Prior Publication Data
US 2022/0345016 A1 Oct. 27, 2022

(30) Foreign Application Priority Data
Apr. 26, 2021 (EP) ..................................... 21170397

(51) Int. Cl.
*H02K 21/02* (2006.01)
*F04D 1/00* (2006.01)
(Continued)

(52) U.S. Cl.
CPC ............. *H02K 21/024* (2013.01); *F04D 1/00* (2013.01); *F04D 13/06* (2013.01); *F04D 29/048* (2013.01); *H02K 7/09* (2013.01)

(58) Field of Classification Search
CPC ............. F16C 32/0476; F16C 32/0497; F16C 32/048; F16C 32/049; H02K 7/09; F04D 29/048; F04D 29/058
See application file for complete search history.

(56) References Cited

U.S. PATENT DOCUMENTS

2018/0326133 A1* 11/2018 Hansen ............... A61M 60/508
2019/0199186 A1* 6/2019 Noh ....................... H02K 21/20

FOREIGN PATENT DOCUMENTS

CN 112546424 A 3/2021
EP 3795836 A1 3/2021
(Continued)

OTHER PUBLICATIONS

Chiba, Electric Motor and Electric Motor System—(JP_6327887_B2_I_MachTrans.pdf), Mar. 2014 (Year: 2014).*
(Continued)

*Primary Examiner* — Kenneth J Hansen
(74) *Attorney, Agent, or Firm* — GLOBAL IP COUNSELORS, LLP

(57) ABSTRACT

An electromagnetic rotary drive includes a rotor including a magnetically effective core surrounded by a stator. The stator has poles arranged around the magnetically effective core and each of the poles is delimited by an end face. The rotor is capable of being magnetically driven without contact in an operating state about an axial direction, and is capable of being magnetically levitated without contact with respect to the stator. The rotor is configured to be magnetically levitated in a radial plane and is passively magnetically stabilized in the axial direction against tilting. The magnetically effective core has a rotor height which is a maximum extension of the magnetically effective core in the axial direction, the rotor height being greater than a stator pole height defined by a maximum extension of the end faces in the axial direction.

15 Claims, 14 Drawing Sheets

(51) Int. Cl.
*F04D 13/06* (2006.01)
*F04D 29/048* (2006.01)
*H02K 7/09* (2006.01)

(56) References Cited

FOREIGN PATENT DOCUMENTS

| | | | |
|---|---|---|---|
| JP | 6327887 B2 | * | 5/2018 |
| JP | 6327887 B2 | | 5/2018 |

OTHER PUBLICATIONS

European Search Report issued Sep. 15, 2021 in corresponding European Application No. 21170397.0.

* cited by examiner

ELECTROMAGNETIC ROTARY DRIVE, A CENTRIFUGAL PUMP AND A PUMP UNIT

CROSS-REFERENCE TO RELATED APPLICATION

This application claims priority to European Patent Application No. 21170397.0, filed Apr. 26, 2021, the contents of which are hereby incorporated herein by reference in their entirety.

BACKGROUND

Field of the Invention

The present disclosure relates to an electromagnetic rotary drive, a centrifugal pump having such an electromagnetic rotary drive, and a pump unit for such a centrifugal pump.

Background Information

Electromagnetic rotary drives are known which are designed and operated according to the principle of the bearingless motor. The term bearingless motor means an electromagnetic rotary drive in which the rotor is levitated completely magnetically with respect to the stator, wherein no separate magnetic bearings are provided. For this purpose, the stator is designed as a bearing and drive stator, which is both the stator of the electric drive and the stator of the magnetic levitation. A magnetic rotating field can be generated with the electrical windings of the stator, which on the one hand exerts a torque on the rotor, which effects its rotation about a desired axis of rotation and which, on the other hand, exerts a shear force, which can be set as desired, onto the rotor so that its radial position can be actively controlled or regulated. Thus, three degrees of freedom of the rotor can be actively regulated, namely its rotation and its radial position (two degrees of freedom). With respect to three further degrees of freedom, namely its position in the axial direction and tilting with respect to the radial plane perpendicular to the desired axis of rotation (two degrees of freedom), the rotor is passively magnetically levitated or stabilized by reluctance forces, i.e., it cannot be controlled. The absence of a separate magnetic bearing with a complete magnetic levitation of the rotor is the property, which gives the bearingless motor its name. In the bearing and drive stator, the bearing function cannot be separated from the drive function.

Such a bearingless motor, which is disclosed for example in U.S. Pat. No. 6,053,705, has proven itself in a large number of applications. Due to the absence of mechanical bearings, the bearingless motor is in particular suitable for pumping, mixing or stirring devices, with which very sensitive substances are conveyed, for example blood pumps, or on which very high demands are made with respect to purity, for example in the pharmaceutical industry or in the biotechnological industry, or with which abrasive or aggressive substances are conveyed, which would very quickly destroy mechanical bearings, for example pumps or mixers for slurry in the semiconductor industry.

A further advantage of the principle of the bearingless motor is the design of the rotor as an integral rotor, which is both the rotor of the electromagnetic rotary drive and the rotor of the pump. In addition to the magnetic levitation without contact, the advantage here is a very compact and space-saving design.

In addition, the principle of the bearingless motor also allows designs, e.g. of centrifugal pumps, in which the rotor can be separated from the stator very easily. This is a very great advantage, because in this way, for example, the rotor or the pump unit comprising the rotor can be designed as a single-use part for single use. Today, such single-use applications often replace processes in which, due to the very high purity requirements, all those components that come into contact with the substances to be treated in the process previously had to be cleaned and sterilized in an elaborate manner, for example by steam sterilization. When designed for single use, those components that come into contact with the substances to be treated are only used exactly once and are then replaced with new, i.e., unused, single-use parts for the next application.

SUMMARY

The pharmaceutical industry and the biotechnological industry can be named as examples here. Solutions and suspensions are frequently produced here that require careful and gentle conveying of substances.

In the pharmaceutical industry, for example in the production of pharmaceutically active substances, very high demands are made on purity, the components which come into contact with the substances often even have to be sterile. Similar demands also result in biotechnology, for example in the production, treatment or cultivation of biological substances, cells or microorganisms, where an extremely high degree of purity has to be ensured in order not to endanger the usability of the product produced. Bioreactors can be named as a further example here in which, for example, biological substitutes for tissue or special cells or other very sensitive substances are cultivated. Centrifugal pumps are also required here in order, for example, to ensure a continuous blending of the nutrient fluid or its continuous circulation in the mixing tank. A very high purity has to be ensured in this respect to protect the substances or the produced products from contamination. Another application example are blood pumps, where of course highest demands are made on purity and furthermore on gentle treatment in particular of red blood cells.

In such applications where a centrifugal pump is designed for single use, the centrifugal pump is typically composed of a single-use device and of a reusable device. The single-use device comprises those components which come into contact with the substances, and which are designed as single-use parts for single use. This is, for example, the pump unit with the pump housing and the rotor arranged therein, which forms the impeller of the centrifugal pump. The reusable device comprises those components which are used permanently. i.e., multiple times, for example the stator of the electromagnetic rotary drive.

In all these applications where the bearingless motor is successfully used, it is in principle possible to design the bearingless motor as an internal rotor. i.e., with an internally located rotor and a stator arranged around it. However, it has been determined that there is still room for improvement in such electromagnetic rotary drives, such as those disclosed in U.S. Pat. No. 6,053,705.

Thus, such devices usually have a relatively low axial stiffness of the magnetic levitation of the rotor, in particular also because the flux density of the magnetic flux in the air gap between the stator and the rotor is rather small, and the gradient of the magnetic flux density at deflections of the rotor in the axial direction is also rather small due to the high dispersion.

Starting from this state of the art, it is therefore an object of the disclosure to disclose an electromagnetic rotary drive which is designed as an internal rotor and which comprises a rotor which can be magnetically driven without contact and which can be magnetically levitated without contact, whereby in particular the axial stiffness of the magnetic stabilization of the rotor is significantly improved. In addition, it is an object of the disclosure to disclose a centrifugal pump which comprises such a rotary drive. Furthermore, a pump unit for such a centrifugal pump is to be disclose by embodiments of the invention, which in particular can also be designed for single use.

The subject matter of the disclosure meeting this object are characterized by the features disclosed herein.

According to an embodiment of the invention, an electromagnetic rotary drive designed as an internal rotor is thus disclosed, with a rotor comprising a ring-shaped or disk-shaped magnetically effective core which is surrounded by a radially externally arranged stator, wherein the stator has a plurality of stator poles which are arranged around the magnetically effective core and each of which in each case is delimited by an end face facing the magnetically effective core of the rotor, wherein the stator is designed as a bearing and drive stator, by which the rotor can be magnetically driven without contact in the operating state about a desired axis of rotation which defines an axial direction, and by which the rotor can be magnetically levitated without contact with respect to the stator, wherein the rotor is actively magnetically levitated in a radial plane perpendicular to the axial direction and is passively magnetically stabilized in the axial direction and against tilting. The magnetically effective core of the rotor has a rotor height which is the maximum extension of the magnetically effective core in the axial direction, wherein the rotor height is greater than a stator pole height which is defined by the maximum extension of the end faces of the stator poles in the axial direction.

Particularly preferably, the magnetically effective core of the rotor is of permanent-magnetic design. i.e., it comprises at least one permanent magnet or it consists of a permanent-magnetic material. Furthermore, it is preferred that each end face of the stator poles has the same extension in the axial direction, so that for each end face their respective extension in the axial direction is equal to the stator pole height.

Due to the fact that the magnetically effective core of the rotor has the rotor height, which is greater than the stator pole height, a concentration of the magnetic flux in the air gap between the end faces and the magnetically effective core of the rotor results. i.e., the magnetic flux density increases in the air gap. Since the axial stiffness of the magnetic stabilization of the rotor increases at least approximately quadratically with the magnetic flux density in the air gap, the axial stiffness increases disproportionately with the rotor height. Thus, the fact that the rotor height is greater than the stator pole height results in an increase in the axial stiffness of the magnetic levitation or stabilization of the rotor.

In order not to reduce the tilting stiffness of the rotor too much, i.e., its resistance to tilting relative to the radial plane, which is perpendicular to the axial direction, it is preferred that the ratio of the outer diameter of the magnetically effective core of the rotor and the rotor height does not fall below the value of 2.8.

In a preferred embodiment, the magnetically effective core comprises a central region which is arranged with respect to the axial direction between a first edge region and a second edge region, and which has a rotor diameter, wherein the first edge region forms a first axial boundary surface of the magnetically effective core which has a first edge diameter, wherein the second edge region forms a second axial boundary surface of the magnetically effective core which has a second edge diameter, and wherein each edge diameter is smaller than the rotor diameter.

In this embodiment, the radially outer region of the magnetic core of the rotor can thus be designed with a lower height—measured in the axial direction—than the region between the first and second axial boundary surfaces. This has the advantage that an increase in the axial stiffness of the magnetic stabilization also results, but a significantly smaller decrease in the tilting stiffness.

Preferably, the central region has a central height which is the extension of the central region in the axial direction, whereby the central height is the same size as the stator pole height. This has the advantage that the radially outer region of the magnetically effective core of the rotor, i.e., that region which is located directly opposite the end faces of the stator poles, has the same extension in the axial direction as the end faces of the stator poles, so that a very high magnetic flux density results in the air gap, which is also advantageous with regard to the torque that drives the rotation of the rotor.

It is a further preferred measure that the magnetically effective core has an outer surface that is not parallel to the axial direction either between the central region and the first axial boundary surface or between the central region and the second axial boundary surface. In this way, it can be realized that the field lines of the magnetic flux between the central region and the two axial boundary surfaces do not emerge from the magnetically effective core of the rotor perpendicular to the axial direction, but at an angle smaller than 90°. Thus, the field lines enter the stator poles further out with respect to the radial direction, which improves the magnetic levitation or stabilization of the rotor.

It is particularly preferred that at least one of the first and the second edge regions is designed in the form of a truncated cone or in the form of a spherical disk or in the form of a paraboloid disk. Due to such embodiments, it can be realized in particular that the outer surface delimiting the magnetically effective core of the rotor does not run parallel to the axial direction both between the central region and the first axial boundary surface and between the central region and the second axial boundary surface, so that here the field lines of the magnetic flux emerge from or enter the magnetically effective core of the rotor at an angle different from 90.

The first and the second edge regions can be designed differently. Thus, for example, the first edge region can be designed in the shape of a truncated cone and the second edge region in the shape of a spherical disk. Of course, it is also possible that the first and the second edge regions are designed in the same way.

According to a first preferred embodiment which is also designated as a radial motor, each stator pole carries at least one concentrated winding such that each concentrated winding is arranged in the radial plane. Thus, in this first embodiment, the windings for generating the electromagnetic fields are arranged in the same plane as the magnetically effective core of the rotor.

According to a second preferred embodiment, the rotary drive is designed as a temple motor, and the stator has a plurality of coil cores, each of which comprises a bar-shaped longitudinal limb which extends in the axial direction from a first end to a second end, and a transverse limb which is arranged at the second end of the longitudinal limb and in the radial plane, and which extends in a radial direction that is perpendicular to the axial direction, wherein each transverse limb forms one of the stator poles, and wherein at least one concentrated winding is arranged on each longitudinal limb, which winding surrounds the respective longitudinal limb. In this embodiment as a temple motor, the windings for generating the electromagnetic fields are thus arranged below the magnetic center plane and aligned in such a way that their coil axis lies in the axial direction in each case.

Furthermore, a centrifugal pump for conveying a fluid is proposed by one embodiment of the invention, which is characterized in that the centrifugal pump comprises an electromagnetic rotary drive designed, the rotor of the electromagnetic rotary drive being designed as the rotor of the centrifugal pump.

Preferably, the centrifugal pump comprises a pump unit with a pump housing comprising an inlet and an outlet for the fluid to be conveyed, wherein the rotor is arranged in the pump housing and comprises a plurality of vanes for conveying the fluid, wherein the pump unit is designed in such a way that the pump unit can be inserted into the stator such that the magnetically effective core of the rotor is surrounded by the stator poles.

Furthermore, a pump unit for a centrifugal pump is proposed by one embodiment of the invention, which is characterized in that the pump unit is designed for a centrifugal pump.

According to a preferred embodiment, the pump housing comprises a base part and a cover which are connected to each other in a sealing manner, wherein the outlet of the pump housing is completely arranged in the base part.

It is also a preferred measure that the rotor has a central bore extending completely through the rotor in the axial direction, so that the axial thrust generated by the vanes is at least partially compensated.

Preferably, the pump unit is designed for detachable connection to the stator of the centrifugal pump according to an embodiment of the invention.

According to a preferred embodiment, the pump unit is designed as a single-use device for single use.

Further advantageous measures and embodiments of the invention result as disclosed herein.

BRIEF DESCRIPTION OF THE DRAWINGS

In the following, the invention is explained in more detail on the basis of embodiments and on the basis of the drawing.

DETAILED DESCRIPTION OF THE EMBODIMENTS

Figure 1:
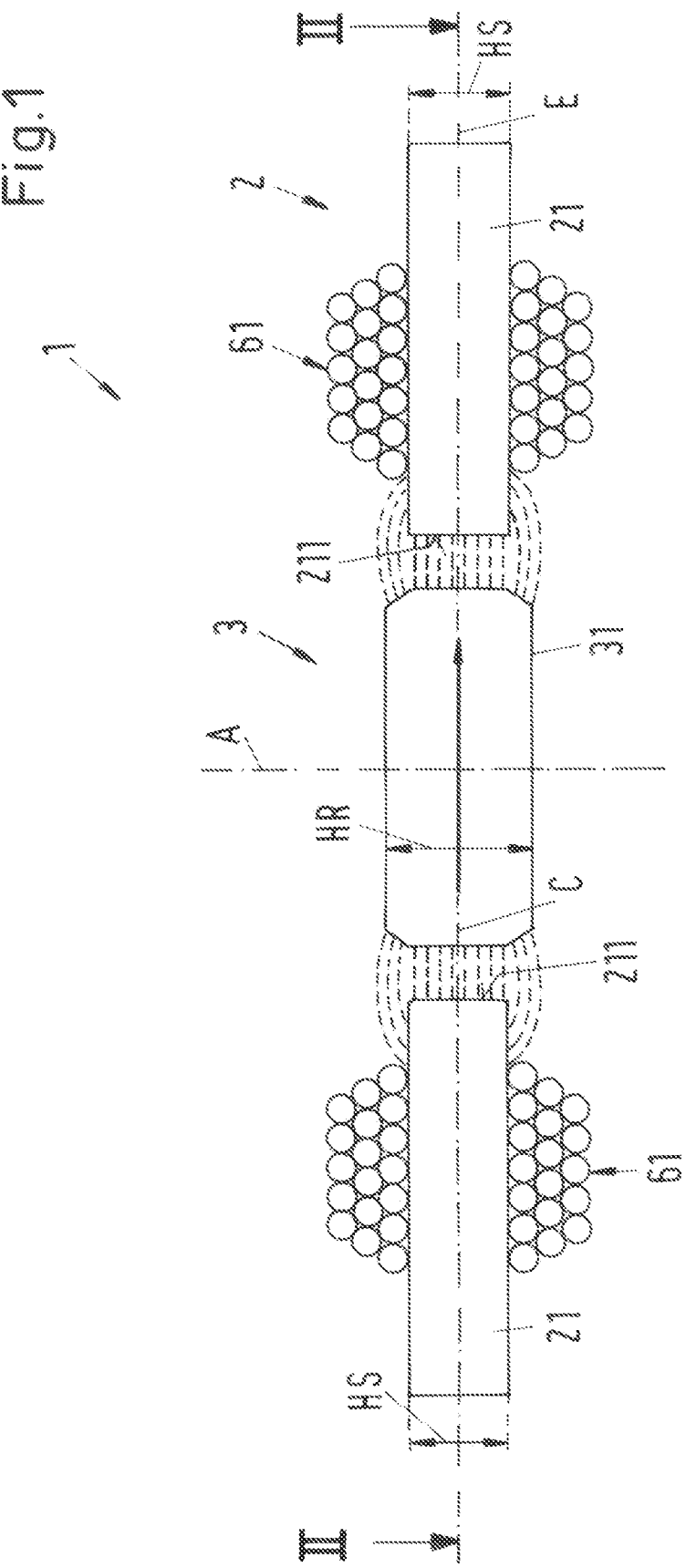
FIG. 1 illustrates a first embodiment of an electromagnetic rotary drive according to the invention in a section in the axial direction, where the section is made along the section line I-I in FIG. 2.
Figure 2:
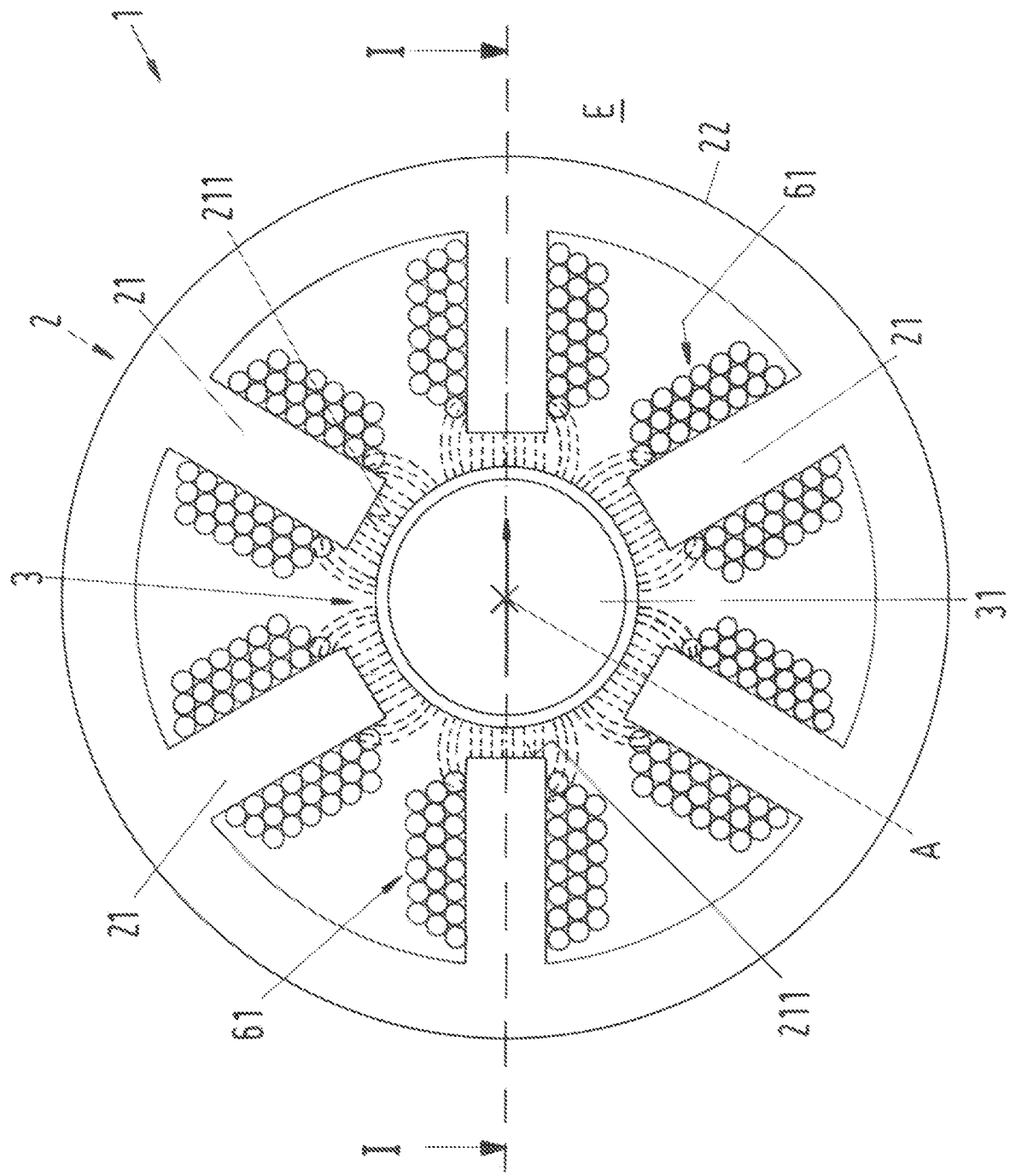
FIG. 2 illustrates a section through the first embodiment in a section perpendicular to the axial direction along the section line II-II in FIG. 1.

FIG. 1 shows a perspective sectional view of a first embodiment of a rotary drive according to the invention, which is designated as a whole by the reference sign. FIG. 1 shows the electromagnetic rotary drive in a section in the axial direction, wherein the section is made along the section line I-I in FIG. 2. For a better understanding. FIG. 2 still shows a section through the electromagnetic rotary drive in a section perpendicular to the axial direction A along the section line II-II in FIG. 1.

The electromagnetic rotary drive is designed as an internal rotor and comprises a stator 2 and rotor 3 which is magnetically levitated without contact with respect to the stator 2. Furthermore, the rotor 3 can be magnetically driven without contact by the stator 2 to rotate about a desired axis of rotation. The desired axis of rotation refers to that axis about which the rotor 3 rotates in the operating state when the rotor 3 is in a centered and not tilted position with respect to the stator 2, as represented in FIG. 1. This desired axis of rotation defines an axial direction A. Usually, the desired axis of rotation defining the axial direction A corresponds to the central axis of the stator 2.

In the following, a radial direction refers to a direction, which stands perpendicular on the axial direction A.

The rotor 3 comprises a magnetically effective core 31, which is designed in a ring-shaped or disk-shaped manner. According to the representation in FIG. 1, the magnetically effective core 31 is designed as a disk and defines a magnetic center plane C. The magnetic center plane C of the magnetically effective core 31 of the rotor 3 refers to that plane perpendicular to the axial direction A in which the magnetically effective core 31 of the rotor 3 is levitated in the operating state when the rotor 3 is not tilted and not deflected in the axial direction A. As a rule, in a disk-shaped or ring-shaped magnetically effective core 31, the magnetic center plane C is the geometric center plane of the magnetically effective core 31 of the rotor 3, which is perpendicular to the axial direction. That plane in which the magnetically effective core 31 of the rotor 3 is levitated in the stator 2 in the operating state is also referred to as the radial plane E. The radial plane defines the x-y plane of a Cartesian coordinate system whose z-axis extends in the axial direction A. If the magnetically effective core 31 of the rotor 3 is not tilted and not deflected with respect to the axial direction (A), the radial plane E coincides with the magnetic center plane C.

FIG. 2 shows a section, which is made in the radial plane E.

The radial position of the magnetically effective core 31 or the rotor 3 refers to the position of the rotor 3 in the radial plane E.

Since it is sufficient for the understanding of the invention, only the magnetically effective core 31 is represented in each case from the rotor 3 in the drawing, e.g., in FIGS. 1 to 10. It is understood that the rotor 3 can, of course, comprise other components such as jackets or encapsulations, which are preferably made of a plastic, or of a metal, or of a metal alloy, or of a ceramic or ceramic material. Furthermore, the rotor 3 can also comprise vanes for mixing, agitating or pumping fluids (see, for example, FIG. 12) or other components.

Figure 5:
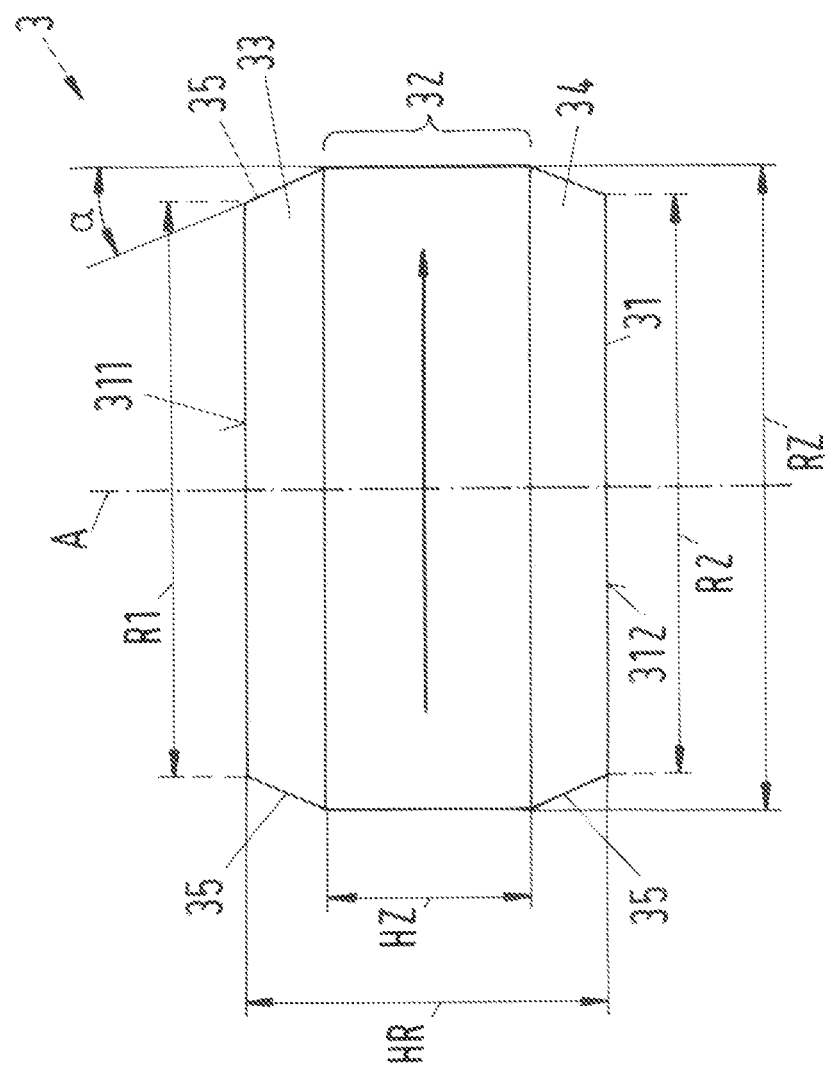
FIG. 5 illustrates the magnetically effective core of the rotor of the first embodiment.

For a better understanding. FIG. 5 still shows a view of the magnetically effective core 31 of the rotor 3.

As is usually the case with an internal rotor 3, the rotor 3 and in particular the magnetically effective core 31 of the rotor 3 is surrounded by the radially outwardly arranged stator 2. The stator 2 comprises a plurality of pronounced stator poles 21—here six stator poles 21—each extending radially inward toward the rotor 3 from a radially outward ring-shaped return 22. Each stator pole 21 is arranged in the radial plane E and is delimited in each case by an end face 211 facing the magnetically effective core 31 of the rotor 3. During operation of the electromagnetic rotary drive, it is the desired position that the magnetically effective core 31 is centered between the end faces 211 of the stator poles 21.

In order to generate the electromagnetic rotating fields required for the magnetic drive and the magnetic levitation of the rotor 3, the stator poles 21 carry windings. In the embodiment described here, the windings are designed as concentrated windings 61, for example, in such a way that exactly one concentrated winding 61 in each case is wound around each stator pole 21, so that each concentrated winding 61 is also arranged in the radial plane E. In the operating state, those electromagnetic rotating fields are generated with these concentrated windings 61 with which a torque is effected on the rotor 3 and with which any adjustable transverse force can be exerted on the rotor 3 in the radial direction, so that the radial position of the rotor 3, i.e. its position in the radial plane E perpendicular to the axial direction A, can be actively controlled or regulated.

The "magnetically effective core 31" of the rotor 3 refers to that region of the rotor 3 which magnetically interacts with the stator poles 21 for torque generation and the generation of magnetic levitation forces.

As already mentioned, the magnetically effective core 31 is designed in a disk-shaped manner. Furthermore, the magnetically effective core 31 is designed in a permanent magnetic manner. For this purpose, the magnetically effective core 31 can comprise at least one permanent magnet, but also several permanent magnets, or—as in the embodiment described here—consist entirely of a permanent magnetic material, so that the magnetically effective core 31 is the permanent magnet. The magnetization of the magnetically effective core of the rotor 3 is represented in FIG. 1, FIG. 2 and FIG. 5 in each case by the arrow without reference sign in the magnetically effective core 31. The magnetically effective core 31 is thus magnetized in the radial direction.

Those ferromagnetic or ferrimagnetic materials, which are magnetically hard, that is which have a high coercive field strength, are typically called permanent magnets. The coercive field strength is that magnetic field strength which is required to demagnetize a material. Within the framework of this application, a permanent magnet is understood as a component or a material, which has a coercive field strength, more precisely a coercive field strength of the magnetic polarization, which amounts to more than 10,000 A/m.

Both the ring-shaped return 22 and the stator poles 21 of the stator 2 are each made of a soft magnetic material because they serve as flux conducting elements to guide the magnetic flux. Suitable soft magnetic materials are, for example, ferromagnetic or ferrimagnetic materials. i.e., in particular iron, nickel-iron, cobalt-iron, silicon iron or Mu-metal. In this case, for the stator 2, a design as a stator sheet stack is preferred, in which the stator poles 21 and the return 22 are designed in sheet metal, i.e., they consist of several thin sheet metal elements, which are stacked. Furthermore, it is possible that the stator poles 21 and the return 22 consist of pressed and subsequently sintered grains of the aforementioned materials. The metallic grains are preferably embedded in a plastic matrix so that they are at least partially insulated from each other, whereby eddy current losses can be minimized. Thus, soft magnetic composites consisting of electrically insulated and compressed metal particles are also suitable for the stator. In particular, these soft magnetic composites, also designated as SMC (Soft Magnetic Composites), can consist of iron powder particles coated with an electrically insulating layer. These SMCs are then formed into the desired shape by powder metallurgy processes.

During operation of the electromagnetic rotary drive 1, the magnetically effective core 31 of the rotor 3 interacts with the stator poles 21 of the stator 2 according to the principle of the bearingless motor described above, in which the rotor 3 can be magnetically driven without contact and can be magnetically levitated without contact with respect to the stator 2. For this purpose, the stator 2 is designed as a bearing and drive stator, with which the rotor 3 can be magnetically driven without contact in the operating state about the desired axis of rotation—i.e., it can be set into rotation—and can be magnetically levitated without contact with respect to the stator 2. Three degrees of freedom of the rotor 3 can be actively regulated, namely its position in the radial plane E and its rotation With respect to its axial deflection from the radial plane E in the axial direction A, the magnetically effective core 31 of the rotor 3 is passively magnetically stabilized by reluctance forces, i.e., it cannot be controlled. Also, with respect to the remaining two degrees of freedom, namely tilts with respect to the radial plane E perpendicular to the desired axis of rotation, the magnetically effective core 31 of the rotor is also passively magnetically stabilized, which will be explained later with reference to FIG. 3 and FIG. 4. Due to the interaction of the magnetically effective core 31 with the stator poles 21, the rotor 3 is thus passively magnetically levitated or passively magnetically stabilized in the axial direction A and against tilting (a total of three degrees of freedom) and actively magnetically levitated in the radial plane (two degrees of freedom).

As is generally the case, an active magnetic levitation is also referred to in the framework of this application as one which can be actively controlled or regulated, for example by the electromagnetic rotating fields generated by the concentrated windings 61. A passive magnetic levitation or a passive magnetic stabilization is one that cannot be controlled or regulated. The passive magnetic levitation or stabilization is based, for example, on reluctance forces, which bring the rotor 3 back again to its desired position when it is deflected from its desired position, e.g., when it is displaced or deflected in the axial direction A or when it is tilted.

A radial levitation or a levitation in a radial manner refers to a levitation of the rotor 3 with which the radial position of the rotor 3 can be stabilized, i.e., a levitation which levitates the rotor 3 in the radial plane E and thus with respect to its radial position.

An axial levitation or a levitation in an axial manner and an axial stabilization or a stabilization in an axial manner, respectively, refers to a levitation or a stabilization of the rotor 3 with which, on the one hand, the position of the rotor 3 is stabilized with respect to the axial direction A and with which, on the other hand, the rotor 3 is stabilized against tilting. Such tilting represents two degrees of freedom and designate deflections in which the momentary axis of rotation of the rotor 3 no longer points exactly in the axial direction A but encloses an angle different from zero with the desired axis of rotation. In the case of a tilt, the magnetic center plane C thus no longer lies in or parallel to the radial plane E, but the magnetic center plane C encloses an angle with the radial plane E that is different from zero.

In the case of a bearingless motor, in contrast to classical magnetic bearings, the magnetic levitation and drive of the motor is realized by electromagnetic rotating fields. Typically, in the bearingless motor, the magnetic drive and levitation function is generated by the superposition of two magnetic rotating fields, which are usually designated as the drive and control fields. These two rotating fields generated with the windings of the stator 2 usually have a pole pair number that differs by one. For example, if the drive field has the pole pair number p, the control field has the pole pair number p+1 or p−1. In this case, tangential forces acting on the magnetically effective core 31 in the radial plane are generated with the drive field, causing a torque, which causes the rotation about the axial direction A. Due to the superposition of the drive field and the control field, it is also possible to generate a transverse force on the magnetically effective core 31 in the radial plane which can be adjusted as desired, with which the position of the magnetically effective core 31 in the radial plane can be regulated. Thus, it is not possible to divide the electromagnetic flux generated by the concentrated windings 61 into an (electro-) magnetic flux that only provides for driving the rotation and an (electro-) magnetic flux that only realizes the magnetic levitation.

To generate the drive field and the control field, it is possible on the one hand to use two different winding systems, namely one to generate the drive field and one to generate the control field. The coils for generating the drive field are then usually designated as drive coils and the coils for generating the control field as control coils. The current impressed in these coils is then designated as the drive current or the control current. On the other hand, it is also possible to generate the drive and levitation function with only one single winding system—as in the embodiment described here—so that there is therefore no distinction between drive and control coils. This can be realized in such a way that the values for the drive current and the control current determined in each case by a control device are added or superimposed by calculation—e.g., with the aid of software—and the resulting total current is impressed into the respective concentrated winding 61. In this case, of course, it is no longer possible to distinguish between control and drive coils. In the first embodiment described here, the last-mentioned variant is realized, i.e., there is no distinction between drive and control coils in the stator 2, but there is only one winding system in each case, in the six concentrated windings 61 of which the calculated sum of the drive and control currents is impressed. However, it is of course also possible to design the electromagnetic rotary drive 1 according to the invention in such a way that two separate winding systems are provided in the stator 2, namely one with separate drive coils and one with separate control coils. Then, for example, two concentrated windings in each case are provided on each stator pole 21, one of which serves as a drive coil and one of which serves as a control coil.

In order to further improve the passive magnetic stabilization of the rotor 3 in particular, according to embodiments of the invention, the magnetically effective core 31 of the rotor 3 is designed in such a way that it has a rotor height HR (see also FIG. 5) which is greater than a stator pole height HS (FIG. 1). The rotor height HR is given by the maximum extension of the magnetically effective core 31 in the axial direction A.

In the first embodiment (see in particular FIG. 5), the magnetically effective core 31 is delimited with respect to the axial direction by a first axial boundary surface 311 and a second axial boundary surface 312, both of which are perpendicular to the axial direction A and thus parallel to each other. In this embodiment, the perpendicular distance between the first axial boundary surface 311 and the second axial boundary surface 312 is the rotor height HR.

The stator pole height HS is defined by the maximum extension of the end faces 211 of the stator poles 21 in the axial direction A. Preferably, all end faces 211 have the same extension in the axial direction, so that each end face 211 has the same maximum extension in the axial direction A, namely the stator pole height HS. Furthermore, it is preferred that each end face 211 is designed in such a way that its axial height is constant when viewed in the circumferential direction. Then, the axial height of each end face 211 is equal to the stator pole height HS.

Due to the design according to embodiments of the invention of the magnetically effective core 31 of the rotor 3, the axial stiffness of the magnetic levitation or the magnetic stabilization of the rotor can be significantly improved, because the higher design of the magnetically effective core 31 with respect to the axial direction A leads to a concentration of the magnetic flux density in the air gap between the end faces 211 of the stator poles 21 and the magnetically effective core 31 of the rotor 3. Due to this concentration of the magnetic flux density in the air gap, a significantly stronger gradient of the magnetic flux density also results at the transition from the (at least approximately) homogeneous field between the end faces 211 and the magnetically effective core 31 into the region of the stray field that prevails above or below the stator poles 21 with respect to the axial direction A. In the Figures, for example in FIG. 1 to FIG. 4, the field lines of the magnetic flux are respectively represented by the dashed lines between the stator poles 21 and the magnetically effective core 31, wherein straight, parallel field lines indicate the region of the homogeneous field and curved field lines indicate the region of the stray fields.

Since the axial stiffness of the magnetic levitation increases quadratically with the magnetic flux density and thus disproportionately with the rotor height HR, a significant improvement in the axial stiffness of the magnetic levitation can be achieved with the embodiment according to the invention. Furthermore, the torque that drives the rotation of the rotor 3 can also be increased with this embodiment by concentrating the magnetic flux in the air gap.

In the embodiment described here (see FIG. 5), the magnetically effective core 31 has a central region 32 which is arranged with respect to the axial direction A between a first edge region 33 and a second edge region 34, wherein both edge regions 33, 34, are directly adjacent to the central region 32. The central region 32 has a diameter which is designated as the rotor diameter RZ. The central region 32 has a central height HZ in the axial direction A, which is smaller than the rotor height HR.

The first edge region 33 forms the first axial boundary surface 311 of the magnetically effective core 31, wherein the first axial boundary surface 311 has a first edge diameter R1 which is its outer diameter. The second edge region 34 forms the second axial boundary surface 312 of the magnetically effective core 31, wherein the second axial boundary surface 312 has a second edge diameter R2 which is its outer diameter. Each of the edge diameters R1 and R2 is smaller than the rotor diameter RZ. The first edge diameter R1 and the second edge diameter R2 can be the same size, as represented in FIG. 5. In other embodiments, the first edge diameter and the second edge diameter can be different sizes.

In the embodiment of the magnetically effective core 31 represented in FIG. 5, the central region 32 has a rectangular profile in an axial section, which has the central height HZ as the height and the rotor diameter RZ as the width.

Particularly preferably, the central region 32 of the magnetically effective core 31 is designed such that the central height HZ is the same as the stator pole height HS.

The first edge region 33 and the second edge region 34 are each designed in the form of a truncated cone, wherein the truncated cone in each case has at its base a diameter corresponding to the rotor diameter RZ and at its axial boundary surface 311, 312, facing away from the base a smaller diameter corresponding to the first edge diameter R1 and the second edge diameter R2, respectively.

Preferably—but not necessarily—the first edge region 311 and the second edge region 312s are designed in the same way.

Such embodiments are also possible in which the first edge region 33 and/or the second edge region 34 are designed in the shape of a circular disk with a diameter corresponding to the first edge diameter R1 or the second edge diameter R2, so that the first edge region 33 and/or the second edge region 34 then have a rectangular profile in an axial section.

However, such embodiments of the magnetically effective core 31 are preferred in which the magnetically effective core 31 has an outer surface which is parallel to the axial direction A neither between the central region 32 and the first axial boundary surface 311 nor between the central region 32 and the second axial boundary surface 312. Thus, such embodiments are preferred in which both the first axial boundary surface 311 and the second axial boundary surface are connected to the central region 32 by transitions 35 that are oblique to the axial direction A or curved.

Due to this measure, the tilting rigidity of the rotor 3, i.e., its resistance to tilting, or its ability to return to the desired position from a tilted position, is significantly improved.

As already mentioned, in the embodiment represented in FIG. 5, the first edge region 33 and the second edge region 34 are each designed in the form of a truncated cone. The inclination of the truncated cone is described by a truncated cone angle α, which is given by the acute angle between the transition and the axial direction A.

In practice, specific combinations of the geometric dimensions have proven to be particularly advantageous.

For the height ratio of the rotor height HR and the central height HZ, the range of 1.2 to 1.6 is preferred, i.e., $1.2 \leq HR/HZ \leq 1.6$, wherein the truncated cone angle α is between 15 degrees and 60 degrees, i.e., $15° \leq α \leq 60°$. It has been shown to be advantageous if the truncated cone angle α is greater the greater the height ratio HR/HZ.

Furthermore, it has been shown to be advantageous if the ratio of the rotor diameter RZ and the rotor height HR is between two and three, i.e., $2 \leq RZ/HR \leq$, whereby this ratio can preferably be selected to be smaller the larger the truncated cone angle α.

Particularly preferably, the height ratio of the rotor height HR and the central height HZ is in the range of 1.3 to 1.5. i.e., $1.3 \leq HR/HZ \leq 1.5$, wherein the truncated cone angle α is between 20 degrees and 30 degrees, i.e., $20° \leq α \leq 30°$ F. or the ratio of the rotor diameter RZ and the rotor height HR, the range of 2.3 to 2.7 is particularly preferred, i.e., $2.3 \leq RZ/HR \leq 2.7$.

Especially preferably, the height ratio of the rotor height HR and the central height HZ is about 1.46, i.e., $HR/HZ = 1.46$, where the truncated cone angle α is about 22.5 degrees, i.e., $α = 22.5°$.

Figure 3:
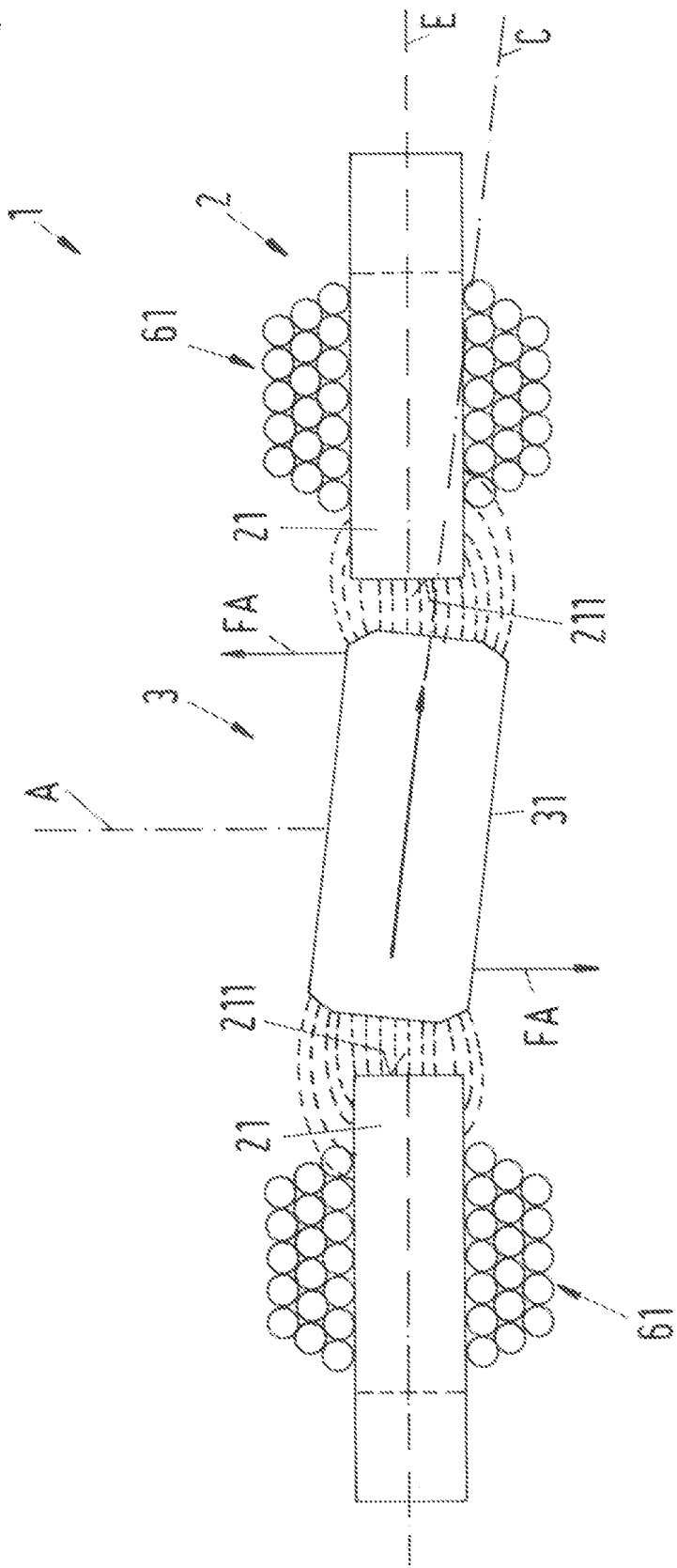
FIG. 3 is as FIG. 1, but with tilted rotor.
Figure 4:
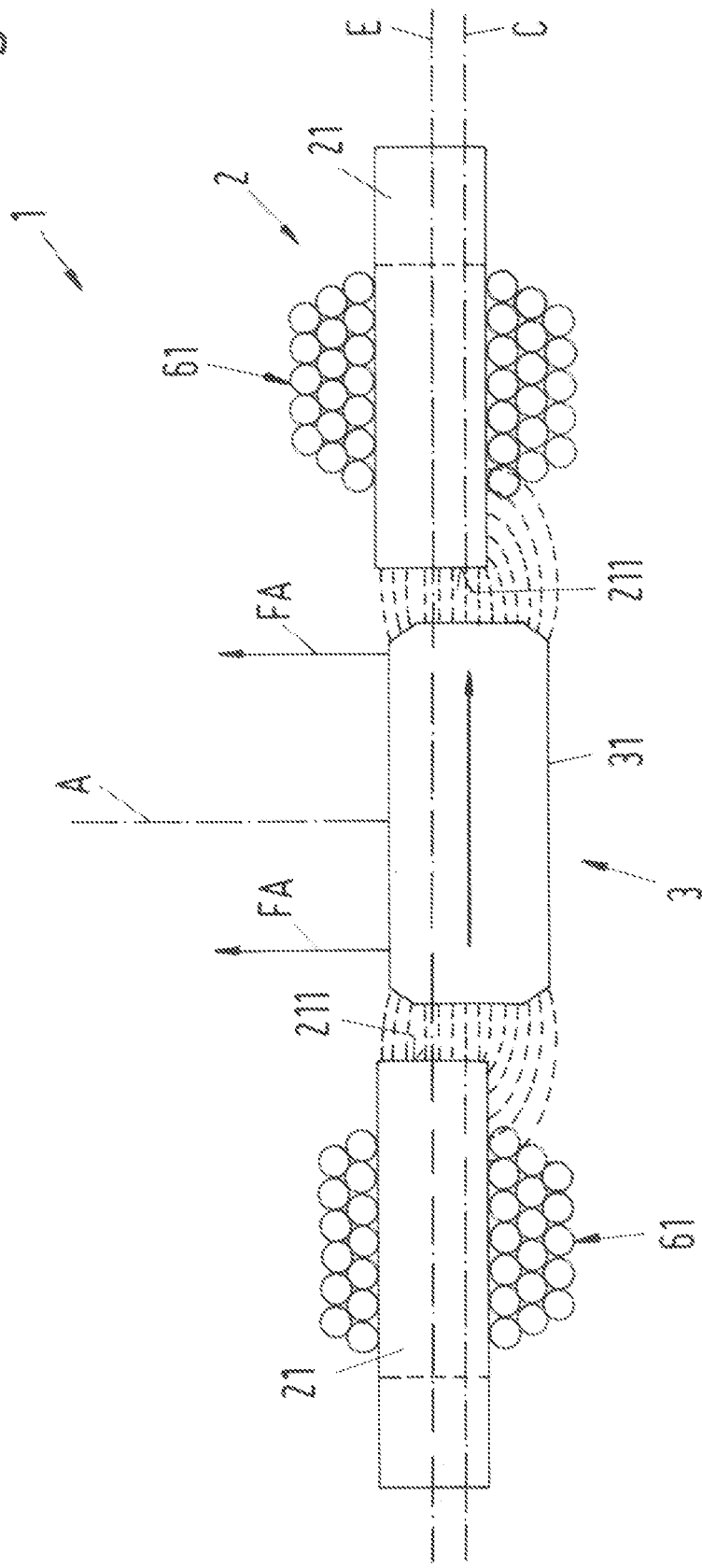
FIG. 4: is as FIG. 1, but with rotor displaced in the axial direction.

In FIG. 3 and FIG. 4, the axial stiffness of the passive magnetic levitation of the rotor 3 against tilting and against displacements of the rotor 3 in the axial direction A, respectively, is illustrated. In this case, the field lines of the magnetic flux between the magnetically effective core of the rotor 3 and the stator poles 21 are again represented by the dashed lines without reference signs.

FIG. 3 shows the magnetically effective core of the rotor in a tilted position in which the magnetic center plane C encloses an angle different from zero with the axial direction A. In this position, a force component FA, which is directed downwards according to the representation, acts in the axial direction A in the region of the magnetically effective core 31 which is opposite the left end face 211 according to the representation, while a force component FA, which is directed upwards according to the representation, acts in the axial direction A in the region of the magnetically effective core 31 which is opposite the right end face 211 according to the representation. Thus, these two force components FA exert a torque on the magnetically effective core 31, which brings it back to its desired position, i.e., to a non-tilted position in which the magnetic center plane C is perpendicular to the axial direction A.

FIG. 4 shows the magnetically effective core 31 of the rotor 3 in a displaced or deflected position with respect to the axial direction A. In this case, the magnetic center plane C is still perpendicular to the axial direction A, but is displaced parallel downward (as represented) with respect to the radial plane E. In this position, a force component FA, which is directed upwards according to the representation, acts in the axial direction A in the region of the magnetically effective core 31 which is opposite to the left end face 211 according to the representation, and a force component FA, which is also directed upwards according to the representation, acts in the axial direction A in the region of the magnetically effective core 31 which is opposite the right end face 211 according to the representation. Thus, these two force components FA exert a force on the magnetically effective core 31 which brings it back to its desired position, in which the magnetic center plane C lies in the radial plane E.

In the following, on the basis of the FIG. 6 to FIG. 9, various variants for the embodiment of the rotor 3 or the magnetically effective core 31 of the rotor 3 are explained. Only the differences with respect to the previous explanations will be discussed. Otherwise, the previous explanations also apply to these variants in the same or in the analogously same way. Furthermore, it is also possible to combine the measures described on the basis of the variants.

Figure 6:
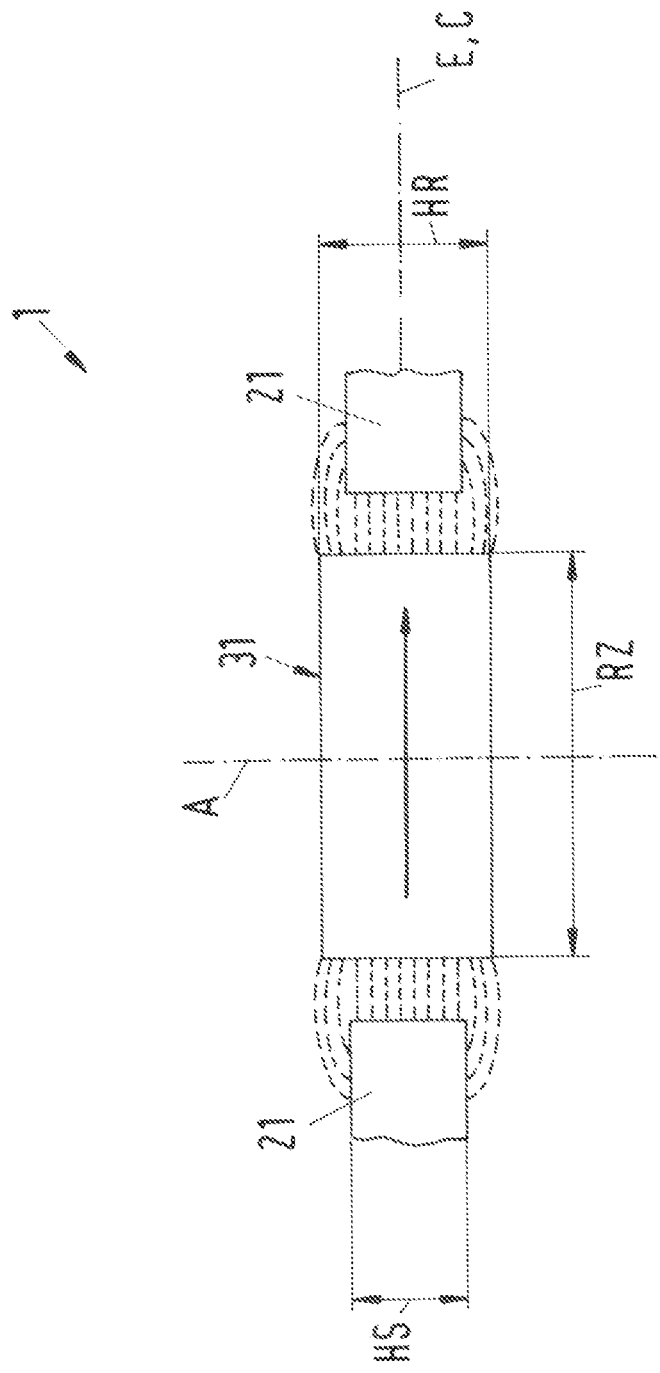
FIG. 6: illustrates a first variant for the magnetically effective core of the rotor in a representation analogous to FIG. 1, FIG. 7: illustrates a second variant for the magnetically effective core of the rotor in a section in the axial direction.

FIG. 6 illustrates a first variant for the magnetically effective core 31 of the rotor 3. In this first variant, the magnetically effective core 31 is designed in its entirety with a height in the axial direction A which is equal to the rotor height HR. In this embodiment, the magnetically effective core 31 does not have any distinct edge regions that could be distinguished from a central region. The magnetically effective core is designed as a circular disk or as a disk of a circular cylinder, wherein this disk has the diameter, which is the rotor diameter RZ, and a height in the axial direction, which is the rotor height HR. Of course, the magnetically effective core 31 can also be designed as a ring-shaped disk.

Figure 7:
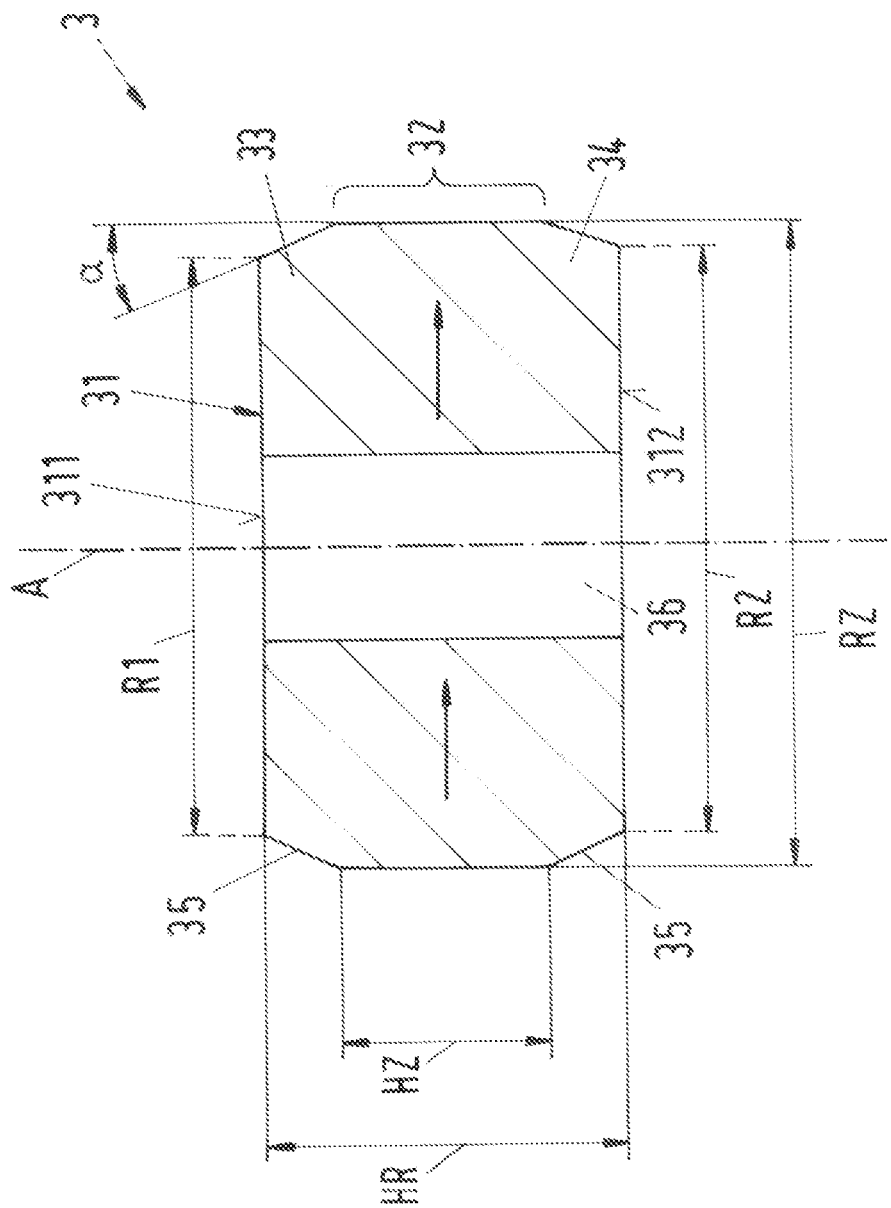

FIG. 7 shows a second variant for the magnetically effective core 31 in a section in the axial direction. The second variant largely corresponds to the embodiment represented in FIG. 5 but has a central bore 36 extending in the axial direction A through the entire magnetically effective core 31 from the first axial boundary surface 311 to the second axial boundary surface 312.

Figure 8:
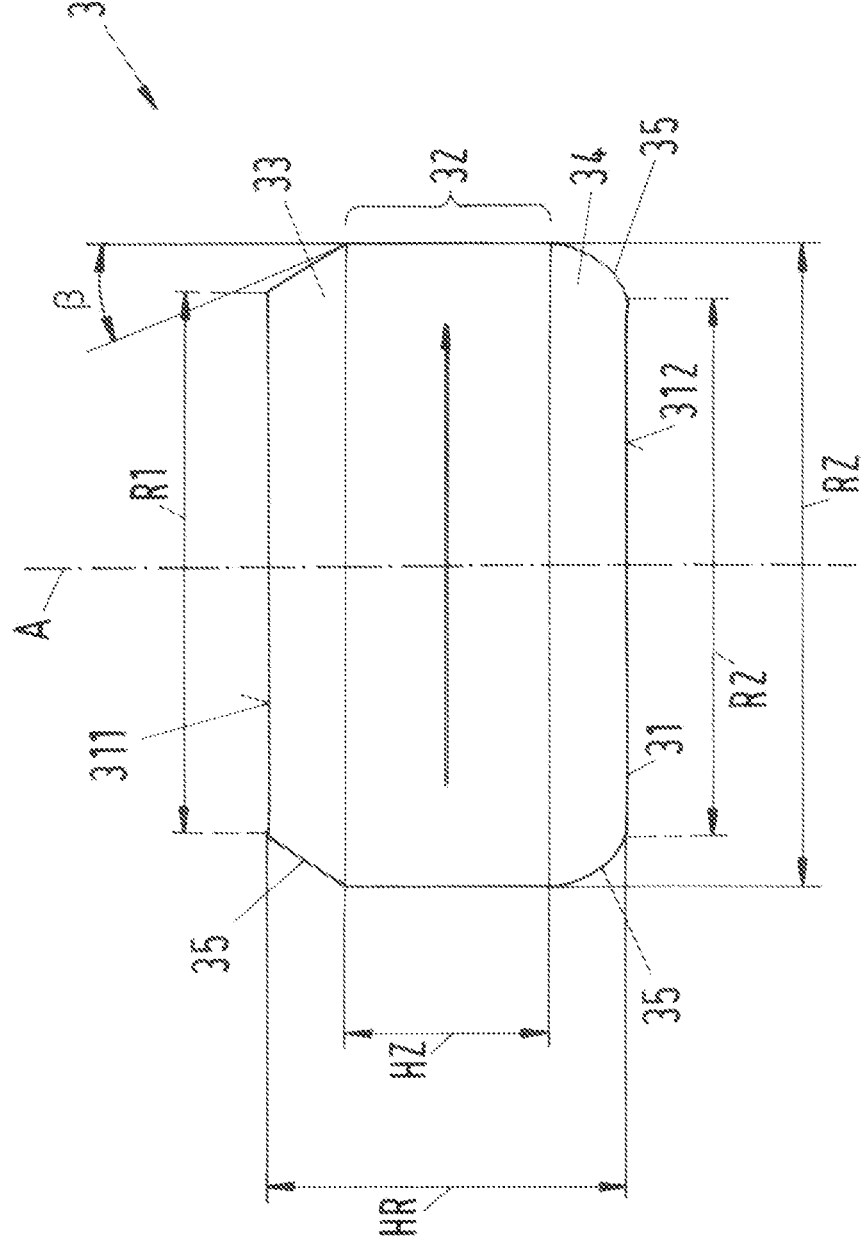
FIG. 8: illustrates a third variant for the magnetically effective core of the rotor.

FIG. 8 shows a third variant for the magnetically effective core 31. The third variant largely corresponds to the embodiment represented in FIG. 5 but differs in the design of the first edge region 33 and the second edge region 34. In the third variant, both edge regions 33, 34 are each designed in the form of a spherical disk or in the form of a paraboloid disk, i.e., the transitions 35 are each designed curved here, for example as a part of a spherical shell or as a part of a paraboloid. The inclination of the transitions 35 can be described, for example, by an inclination angle β, which can be defined in the analogously same way as the truncated cone angle α. Thus, for example, the inclination angle β is the acute angle which a tangent to the transition 35 makes with the axial direction A. The same explanations apply analogously to the inclination angle β as to the truncated cone angle α.

Figure 9:
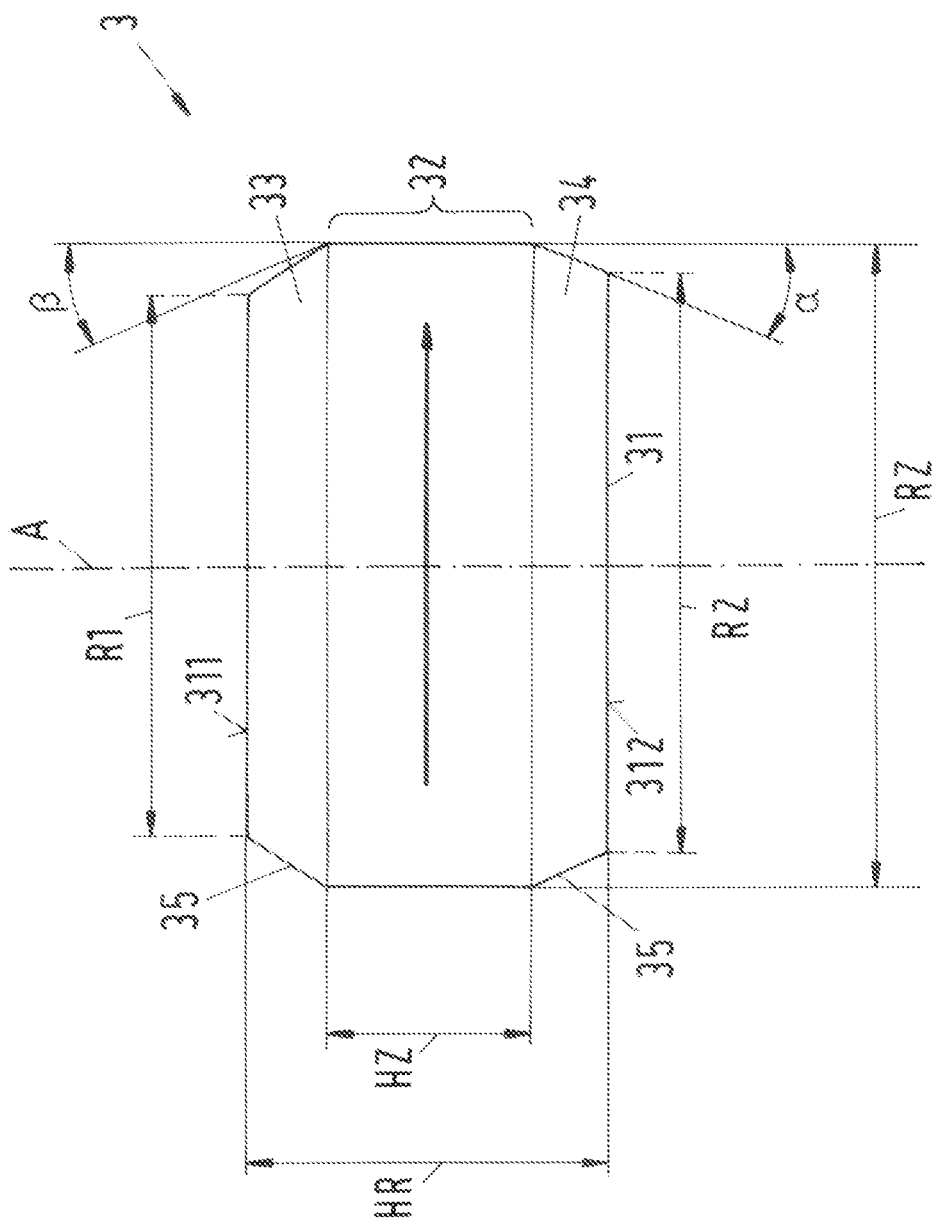
FIG. 9: illustrates a fourth variant for the magnetically effective core of the rotor.

FIG. 9 shows a fourth variant for the magnetically effective core 31. The fourth variant largely corresponds to the embodiment represented in FIG. 5 but differs in the design of the first edge region 33. In the fourth variant, only the second edge region 34 is designed in the form of a truncated cone, while the first edge region is designed in the form of a spherical disk or in the form of a paraboloid disk.

Figure 10:
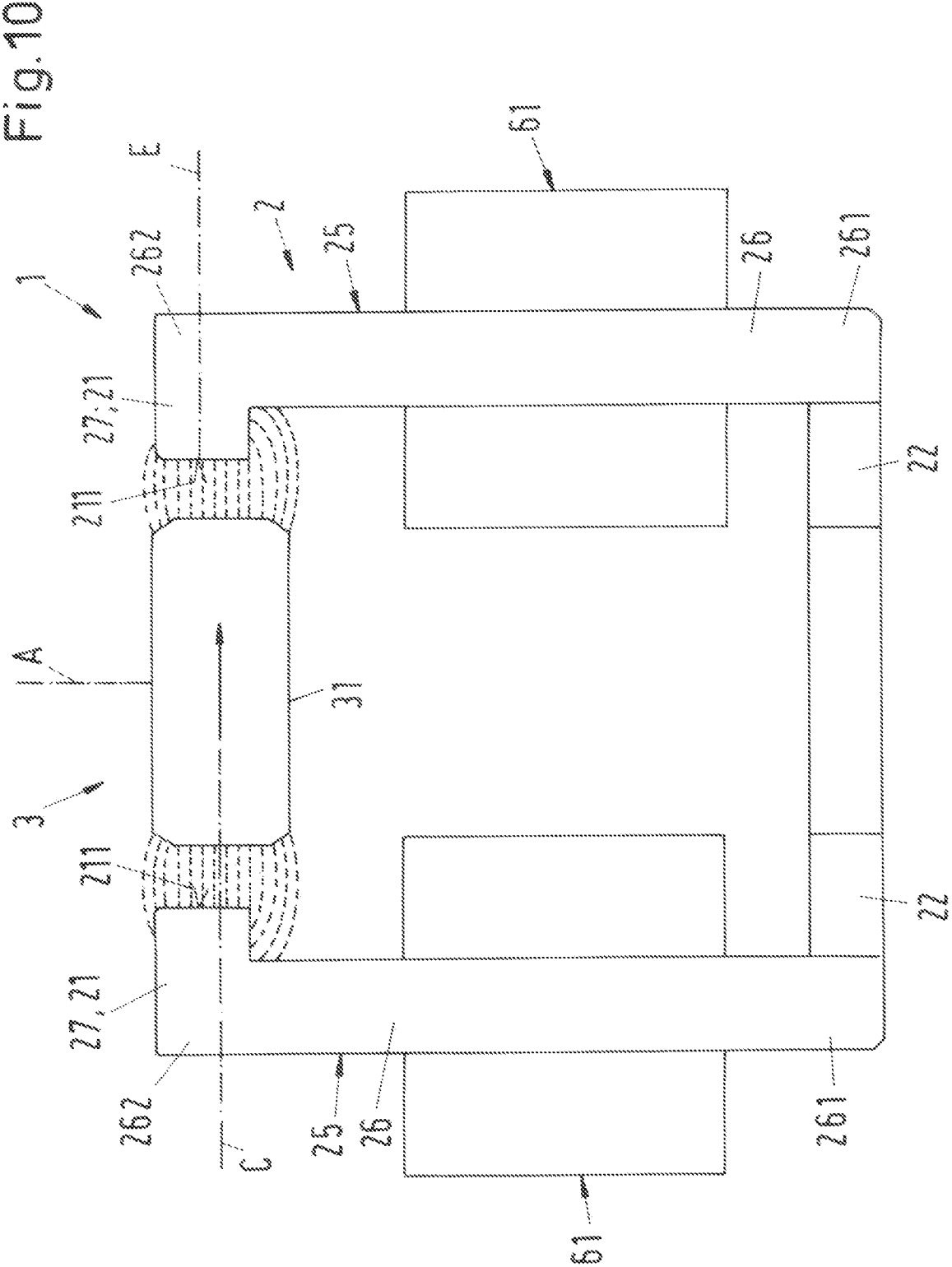
FIG. 10 illustrates a second embodiment of an electromagnetic rotary drive according to the invention in a section in the axial direction.

FIG. 10 shows a second embodiment of an electromagnetic rotary drive according to the invention in a section in the axial direction A. For a better understanding, FIG. 11 still shows a plan view on the second embodiment from the axial direction A.

In the following, only the differences to the first embodiment will be discussed. The same parts or parts equivalent in function of the second embodiment are designated with the same reference signs as in the first embodiment or its variants. In particular, the reference signs have the same meaning as already explained in connection with the first embodiment. It is understood that all previous explanations of the first embodiment and its variants also apply in the same way or in the analogously same way to the second embodiment.

In the second embodiment, the electromagnetic rotary drive 1 is designed as a temple motor. The electromagnetic rotary drive 1 comprises the stator, wherein the stator 2 has a plurality of coil cores 25, each of which comprises a bar-shaped longitudinal limb 26 extending in the axial direction A from a first end 261 to a second end 262, and a transverse limb 27 which is arranged at the second end 262 of the longitudinal limb 26. Each transverse limb 27 extends in the radial direction towards the rotor 3. Thus, each coil core 25 has the shape of an L, wherein the longitudinal limbs 26 each form the long limb of the L extending in the axial direction A, and the transverse limbs 27 extending perpendicular to the longitudinal limbs 26 in the radial direction toward the rotor 3 each form the short limb of the L.

Each transverse limb 27 forms one of the stator poles 21. In contrast to the first embodiment, which is designed as a radial motor, the concentrated windings 61 are not carried by the stator poles 21, but at least one of the concentrated windings 61 is arranged on each longitudinal limb 26, surrounding the respective longitudinal limb 26.

When the magnetically effective core 31 of the rotor 3 is in its desired position during operation, the magnetically effective core 31 is centered between the stator poles 21, which are formed by the transverse limbs 27, so that the stator poles 21 are arranged in the magnetic center plane C and in the radial plane E, respectively (in this case, these two planes are the same). According to the representation, the concentrated windings are arranged below the radial plane E and are aligned such that their coil axes extend in the axial direction A.

All first ends 261 of the longitudinal limbs 26—these are the lower ends according to the representation in FIG. 10—are connected to each other by the return 22. The return 22 is preferably designed in a ring-shaped manner. Such embodiments are possible (see FIG. 10) in which the return 22 extends radially inwardly along all first ends 261 of the longitudinal limbs. However, it is also possible that the return 22 has a plurality of recesses along its circumference, each of which receives one of the first ends 262.

Furthermore, a centrifugal pump 100 for conveying a fluid is proposed by an embodiment of the invention, which is characterized in that the centrifugal pump 100 comprises an electromagnetic rotary drive 1 designed according to the invention, wherein the rotor 3 of the electromagnetic rotary drive 1 is designed as the rotor 3 of the centrifugal pump 100.

Figure 12:
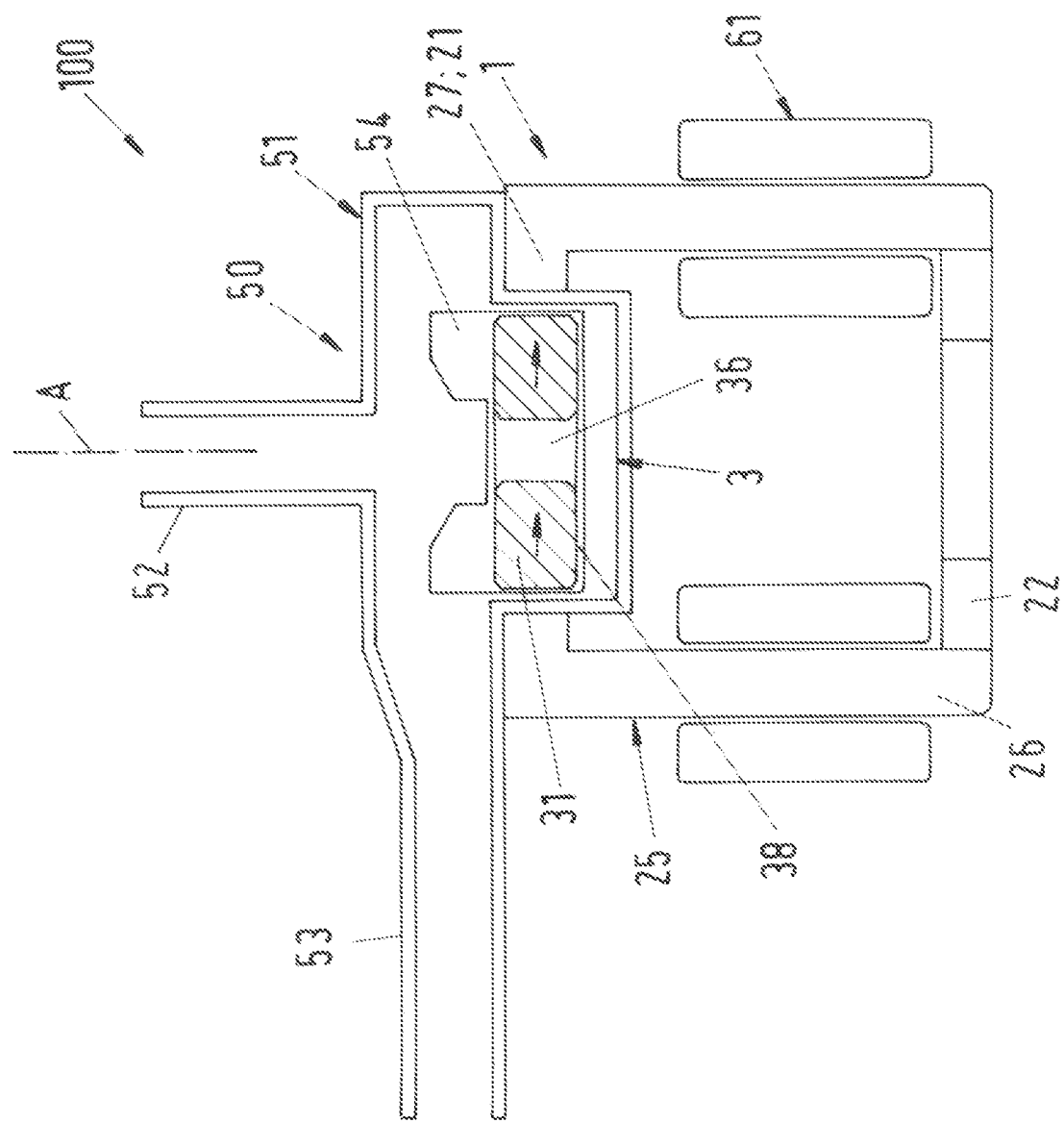
FIG. 12 illustrates an embodiment of a centrifugal pump according to the invention in a section in the axial direction.

FIG. 12 shows an embodiment of a centrifugal pump according to the invention, which is designated as a whole by the reference sign 100, in a section in the axial direction A.

Figure 11:
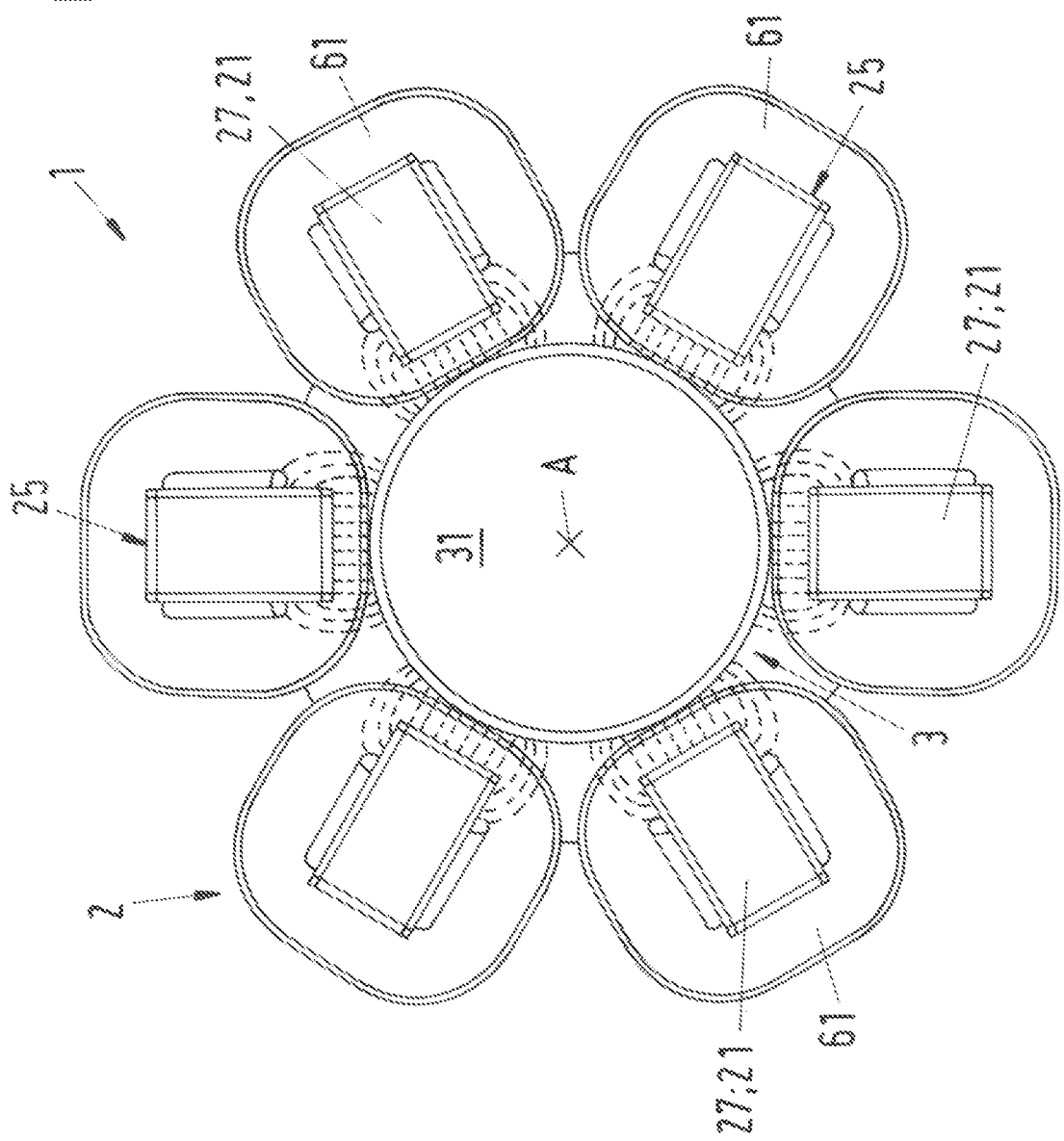
FIG. 11 illustrates a plan view on the second embodiment from the axial direction.

In this embodiment of the centrifugal pump 100, the electromagnetic rotary drive 1 is designed as a temple motor, i.e., according to the second embodiment (FIG. 10, FIG. 11).

The centrifugal pump 100 comprises a pump unit 50 with a pump housing 51 comprising an inlet 52 and an outlet 53 for the fluid to be conveyed, wherein the rotor 3 is arranged in the pump housing 51 and comprises a plurality of vanes 54 for conveying the fluid. The pump unit 50 is designed in such a way that the pump unit 50 can be inserted into the stator 2 such that the magnetically effective core of the rotor 31 is surrounded by the stator poles 21.

It is an advantageous aspect that the rotor 3 is designed as an integral rotor, because it is both the rotor 3 of the electromagnetic rotary drive 1 and the rotor 3 of the centrifugal pump 100, with which the fluid is conveyed. In total, the rotor 3 thus fulfills three functions in one. It is the rotor 3 of the electromagnetic drive 1, it is the rotor 3 of the magnetic levitation, and it is the impeller with which the fluid or fluids are acted upon. This embodiment as an integral rotor offers the advantage of a very compact and space-saving design.

Figure 13:
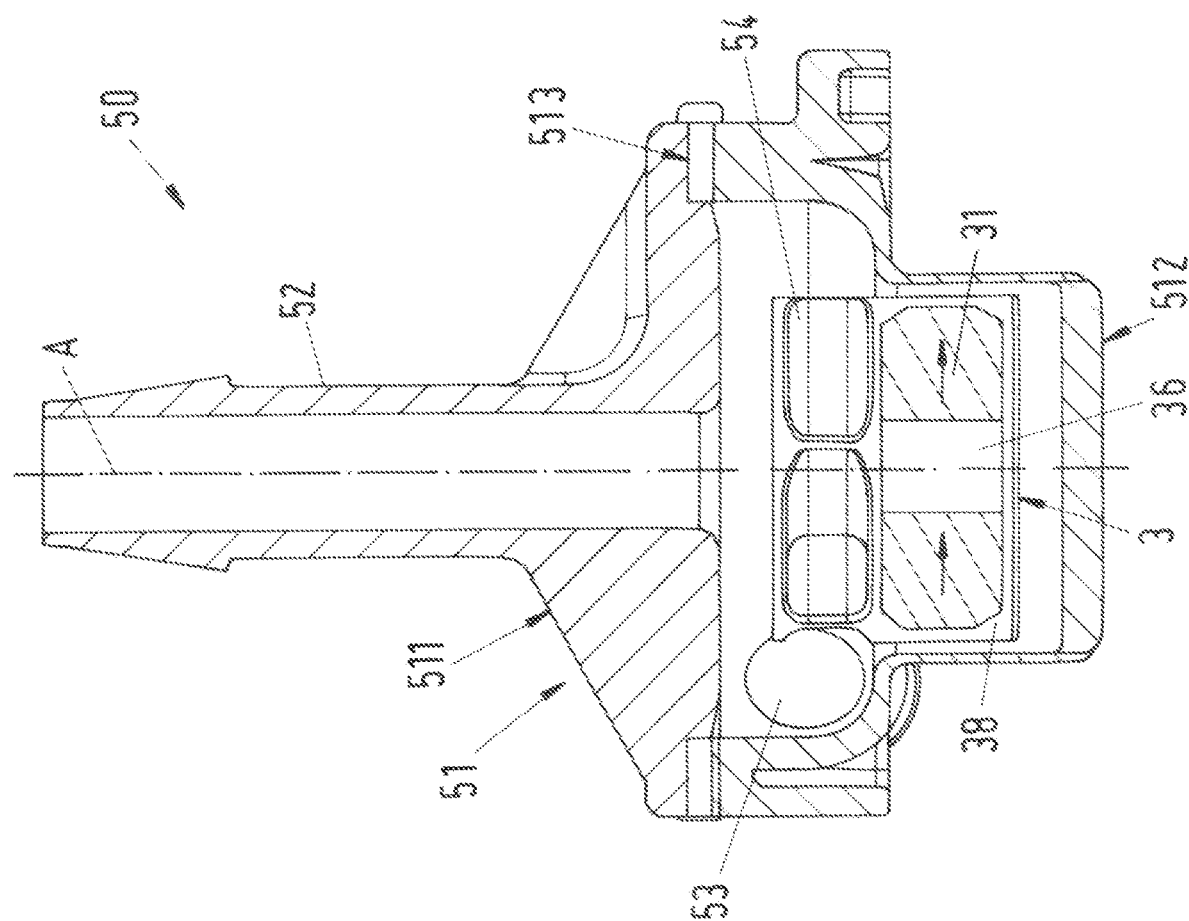
FIG. 13 illustrates the pump unit of the centrifugal pump from FIG. 12 in an axial section along the section line XIII-XIII in FIG. 14.
Figure 14:
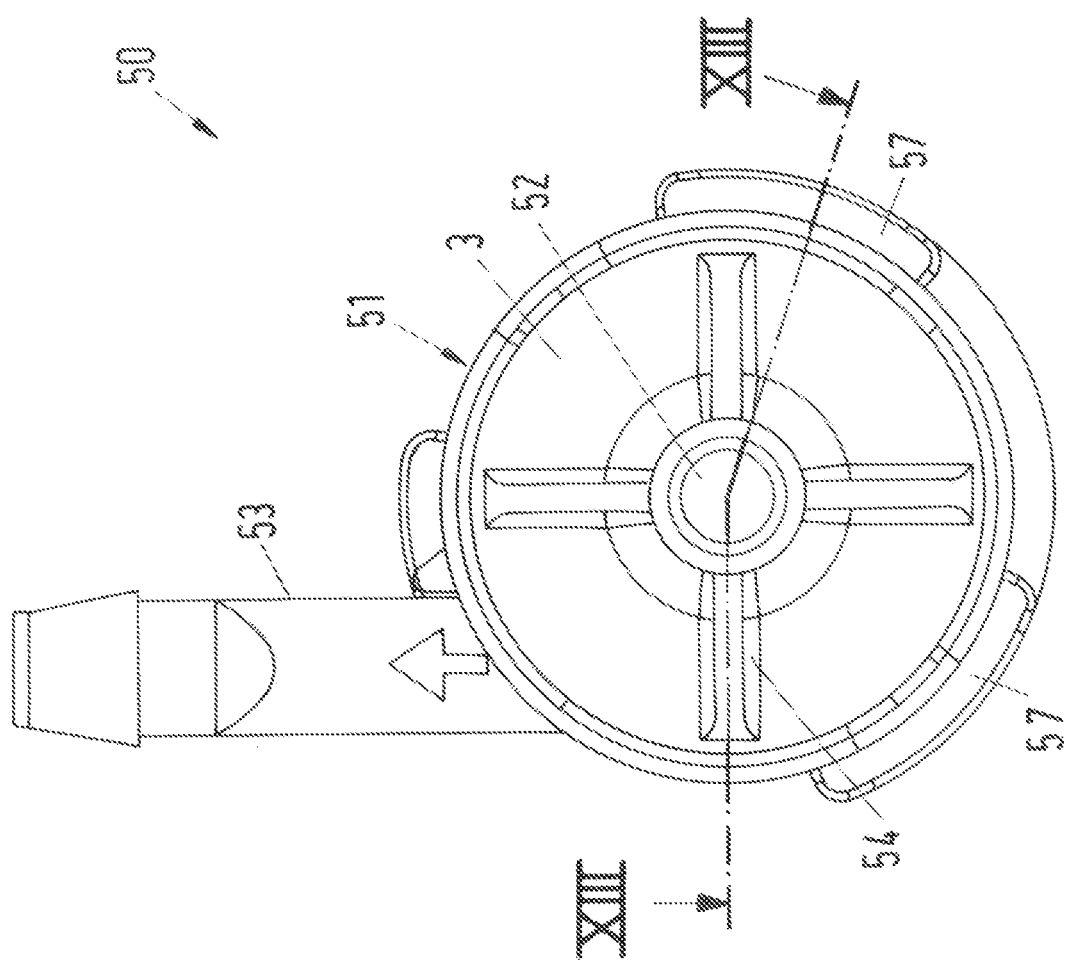
FIG. 14 illustrates a plan view on the pump unit from FIG. 13 from the axial direction.

For a better understanding, FIG. 13 still shows a slightly more detailed representation of the pump unit 50 of the centrifugal pump 100 in a section along the section line XIII-XIII in FIG. 14. FIG. 14 shows a plan view on the pump unit 50 from the axial direction A.

The pump housing 51 of the pump unit comprises a base part 512 and a cover 511, which are connected to each other in a sealing manner, wherein the outlet 53 of the pump housing 51 is completely arranged in the base part 512. The cover 511 comprises the inlet 52, which extends in the axial direction A, so that the fluid flows to the rotor 3 from the axial direction A.

In this regard, it is also a substantial aspect that the outlet 53 is completely arranged in the base part 512 so that the outlet 53 does not have any parting lines, welding lines or similar joints.

Any methods known per se are suitable for a connection of the cover 511 and the base part 512 in a sealing manner. Thus, for example, the base part 512 and the cover 511 can be connected to each other by a screw connection or by a click connection or by a snap-in connection, by gluing or by various types of welding, for example by infrared welding. Depending on the type of connection, it can be advantageous to provide a sealing element 513, for example an O-ring, between the base part 512 and the cover 511.

The rotor 3 comprises the plurality of vanes 54 for conveying the fluid. In the case of the embodiment described here, a total of four vanes 54 are provided, whereby this number has an exemplary character. The rotor 3 further comprises a jacket 38 with which the magnetically effective core 31 of the rotor 3 is enclosed and preferably hermetically encapsulated so that the magnetically effective core 31 of the rotor 3 does not come into contact with the fluid to be conveyed. All vanes 54 are arranged on the jacket 38 and arranged equidistantly with respect to the circumferential direction of the rotor 3. Each vane 54 extends outward in the radial direction and is connected to the jacket 38 in a torque-proof manner. The vanes 54 can be separate components that are then fixed to the jacket 38. Of course, it is also possible that all of the vanes 54 are an integral part of the jacket 38. i.e., that the jacket 38 is designed with all of the vanes 54 as a single piece. The rotor 3 with the vanes 54 forms the impeller or the impeller of the centrifugal pump 100, with which the fluid or fluids are acted upon.

Preferably, the rotor 3 comprises the central bore 36, which extends completely through the rotor 3 in the axial direction A. At least a partial axial thrust compensation can be ensured by this central bore 36, so that the passive magnetic axial levitation of the rotor 3 is relieved.

Depending on the application, for example, if the centrifugal pump is used as a blood pump, it is preferred if the pump housing 51 of the pump unit 50 as well as the jacket 38 and the vanes 54 are made of one or more plastics. Suitable plastics are: Polyethylene (PE), Low Density Polyethylene (LDPE), Ultra Low Density Polyethylene (ULDPE). Ethylene Vinyl Acetate (EVA). Polyethylene Terephthalate (PET), Polyvinyl Chloride (PVC), Polypropylene (PP). Polyurethane (PU), Polyvinylidene Fluoride (PVDF), Acrylonitrile Butadiene Styrene (ABS), Polyacryl. Polycarbonates (PC), Polyetheretherketone (PEEK) or Silicones. For many applications, the materials known under the brand name Teflon, polytetrafluoroethylene (PTFE) and perfluoroalkoxy polymers (PFA), are also suitable plastics.

Preferably, the pump unit 50 is designed for detachable connection to the stator 2 of the centrifugal pump 100. For this purpose, several lugs 57 can be provided on the pump housing 51, for example, which can cooperate with the stator 2 in the form of a bayonet connection.

In a particularly preferred embodiment, the pump unit 50 is designed as a single-use device for single use, which can be inserted into the stator 2 designed as a reusable device. Then, the centrifugal pump 100 is composed of the pump unit 50, which is designed as a single-use device for single use, and the stator 2, which is designed as a reusable device designed for multiple use. The stator 2 typically also comprises the control, regulation and supply units of the electromagnetic rotary drive 1.

The term "single-use device" and other compositions with the component "single-use" refer to such components or parts that are designed for single-use, i.e., that can be used only once according to their intended purpose and are then disposed of. A new, previously unused single-use part must then be used for a new application. In the conception or design of the single-use device, it is therefore a substantial aspect that the single-use device can be assembled with the reusable device to form the centrifugal pump in the simplest possible manner. The single-use device should therefore be able to be replaced in a very simple manner without the need for a high level of assembly work. Particularly preferably, the single-use device should be able to be assembled with and separated from the reusable device without the use of tools. The pump unit 50 can be designed as such a single-use device.

The centrifugal pump $1(x)$ can be used, for example, in the medical industry as a blood pump, or can find use in the pharmaceutical industry or in the biotechnology industry. The centrifugal pump 100 is especially suitable for such applications in which a very high degree of purity or sterility of those components that come into contact with the substances to be mixed is substantial.

It is understood that the centrifugal pump 100 according to the invention for conveying fluids can also be designed with an electromagnetic rotary drive 1, which is designed according to the first embodiment (FIG. 1, FIG. 2), i.e., as a radial motor, in which the windings 61 are arranged on the stator poles 21 in the radial plane E.

What is claimed is:

1. An electromagnetic rotary drive configured as an internal rotor, comprising:
   the internal rotor comprising a ring-shaped or disk-shaped magnetically effective core surrounded by a radially externally arranged stator, the stator having a plurality of stator poles arranged around the magnetically effective core and each of the plurality of stator poles being delimited by an end face facing the magnetically effective core of the rotor, the stator being a bearing and drive stator, by which the rotor is capable of being magnetically driven without contact in an operating state about an axis of rotation defining an axial direction, and by which the rotor is capable of being magnetically levitated without contact with respect to the stator, the rotor configured to be actively magnetically levitated in a radial plane perpendicular to the axial direction and passively magnetically stabilized in the axial direction against tilting, the magnetically effective core of the rotor having a rotor height which is a maximum extension of the magnetically effective core in the axial direction, the rotor height being greater than a stator pole height defined by a maximum extension of the end faces of the stator poles in the axial direction,
   the magnetically effective core comprising a central region arranged with respect to the axial direction between a first edge region and a second edge region, and has a rotor diameter, the first edge region forms a first axial boundary surface of the magnetically effective core and has a first edge diameter, the second edge region forms a second axial boundary surface of the magnetically effective core which and has a second edge diameter, and each of the first and second edge diameters being smaller than the rotor diameter.

2. The rotary drive according to claim 1, wherein the central region has a central height which is the extension of the central region in the axial direction, and the central height is a same size as the stator pole height.

3. The rotary drive according to claim 2, wherein the magnetically effective core has an outer surface that is not parallel to the axial direction either between the central region and the first axial boundary surface or between the central region and the second axial boundary surface.

4. The rotary drive according to claim 1, wherein at least one of the first and second edge regions is a truncated cone or a spherical disk or a paraboloid disk.

5. The rotary drive according to claim 1, wherein the first edge region and the second edge region have a same configuration.

6. The rotary drive according to claim 1, wherein each stator pole carries at least one concentrated winding such that each concentrated winding is arranged in the radial plane.

7. The rotary drive according to claim 1, wherein the rotary drive is a temple motor, and the stator has a plurality of coil cores, each of the plurality of coil cores comprises a bar-shaped longitudinal limb extending in the axial direction from a first end to a second end and a transverse limb arranged at the second end of the longitudinal limb and in the radial plane, and extends in a radial direction which is perpendicular to the axial direction, each transverse limb forms one of the stator poles, and at least one concentrated winding is arranged on each longitudinal limb, which surrounds a respective longitudinal limb.

8. A centrifugal pump for conveying a fluid, comprising:
the electromagnetic rotary drive according to claim 1, the rotor of the electromagnetic rotary drive being the rotor of the centrifugal pump.

9. The centrifugal pump according to claim 8, further comprising a pump unit with a pump housing comprising an inlet and an outlet for the fluid to be conveyed, the rotor is disposed in the pump housing and comprising a plurality of vanes for conveying the fluid, the pump unit configured to be inserted into the stator such that the magnetically effective core of the rotor is surrounded by the stator poles.

10. The rotary drive according to claim 1, wherein each of the first and second axial boundary surfaces extends transverse to the axial direction.

11. A pump unit for a centrifugal pump, the pump unit being configured for the centrifugal pump according to claim 9.

12. The pump unit according to claim 11, wherein the pump housing comprises a base part and a cover connected to each other in a sealing manner, and the outlet of the pump housing is completely arranged in the base part.

13. The pump unit according to claim 11, wherein the rotor has a central bore extending completely through the rotor in the axial direction.

14. The pump unit according to claim 11, wherein the pump unit is configured to be detachably connected to the stator of the centrifugal pump.

15. The pump unit according to claim 11, wherein the pump unit is a single-use device for single use.

* * * * *